(12) United States Patent
Ernst et al.

(10) Patent No.: US 12,129,217 B2
(45) Date of Patent: Oct. 29, 2024

(54) CONTINUOUS PROCESS FOR THE PRODUCTION OF ALKANES

(71) Applicant: BASF SE, Ludwigshafen am Rhein (DE)

(72) Inventors: Martin Ernst, Ludwigshafen am Rhein (DE); Johann-Peter Melder, Ludwigshafen am Rhein (DE); Tatjana Huber, Ludwigshafen am Rhein (DE); Markus Dierker, Düsseldorf (DE)

(73) Assignee: BASF SE, Ludwigshafen am Rhein (DE)

( * ) Notice: Subject to any disclaimer, the term of this patent is extended or adjusted under 35 U.S.C. 154(b) by 114 days.

(21) Appl. No.: 17/922,798

(22) PCT Filed: Apr. 26, 2021

(86) PCT No.: PCT/EP2021/060809
§ 371 (c)(1),
(2) Date: Nov. 2, 2022

(87) PCT Pub. No.: WO2021/224045
PCT Pub. Date: Nov. 11, 2021

(65) Prior Publication Data
US 2023/0159410 A1    May 25, 2023

(30) Foreign Application Priority Data
May 6, 2020    (EP) .................... 20173243.5

(51) Int. Cl.
*C07C 1/22*    (2006.01)
*A61K 8/31*    (2006.01)
*C07C 1/20*    (2006.01)

(52) U.S. Cl.
CPC .................. *C07C 1/22* (2013.01); *A61K 8/31* (2013.01); *C07C 1/20* (2013.01);
(Continued)

(58) Field of Classification Search
CPC ......... C07C 1/22; C07C 1/20; C07C 2521/08; C07C 2523/755; A61K 8/31; A61K 2800/805
See application file for complete search history.

(56) References Cited

U.S. PATENT DOCUMENTS

| 2,060,267 A | 11/1936 | Toussaint |
| 3,426,080 A | 2/1969 | Tummes et al. |

(Continued)

FOREIGN PATENT DOCUMENTS

| DE | 102010033523 A1 | 2/2012 |
| GB | 1051826 A | 12/1966 |
| WO | 2007/068371 A1 | 6/2007 |

OTHER PUBLICATIONS

Pines et al. ; "Specificity of Nickel Catalysts. Effect of Organic Additives upon the Reductive Dehydroxymethylation and Dehydroxylation of Primary Alcohols", ACS Publications, 1955. (Year: 1955).*

(Continued)

*Primary Examiner* — Ali Z Fadhel
(74) *Attorney, Agent, or Firm* — Faegre Drinker Biddle & Reath LLP

(57) ABSTRACT

Continuous reductive dehydroxymethylation process for the preparation of alkanes from primary aliphatic alcohols, having 3 to 25 carbon atoms, in the presence of hydrogen and a catalyst in a reactor at a pressure of $\geq 2$ bar, characterized in that the dehydroxymethylation takes place in the vapor phase.

15 Claims, 2 Drawing Sheets

Figure 1:
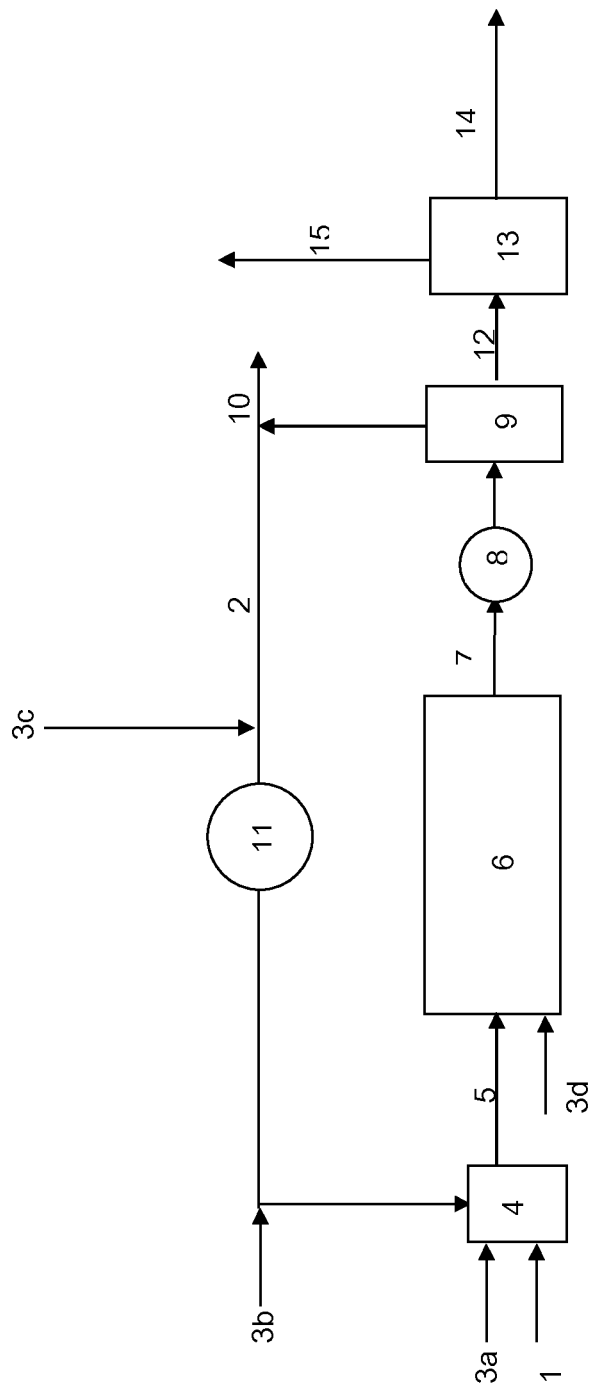

(52) U.S. Cl.
CPC .... *A61K 2800/805* (2013.01); *C07C 2521/08* (2013.01); *C07C 2523/755* (2013.01)

(56) References Cited

U.S. PATENT DOCUMENTS

| | | | | |
|---|---|---|---|---|
| 2008/0269352 | A1* | 10/2008 | Falkowski | A61Q 19/00 |
| | | | | 514/762 |
| 2019/0262819 | A1* | 8/2019 | Dong | C07C 1/2076 |
| 2019/0263729 | A1* | 8/2019 | Bischof | C07C 67/297 |

OTHER PUBLICATIONS

Badin, Elmer J., "Catalytic Dehydrogenation. I. Catalytic Conversion of Alcohols into Aldehydes, Paraffins and Olefins", Journal of the American Chemical Society, vol. 65, Issue 10, Oct. 1, 1943, pp. 1809-1813.

Bieri et al., "Valence ionization energies of hydrocarbons", Helvetica Chimica Acta, vol. 60, Issue 7, Nov. 2, 1977, pp. 2213-2233.

Elvers et al., "Fixed-Bed Reactors", Ullmann's Encyclopedia of Industrial Chemistry, 5th Edition, Principles of chemical Reaction Engineering and Plant Design, vol. B4, 1992, pp. 199-238.

European Search Report for EP Patent Application No. 20173243.5, Issued on Nov. 10, 2020, 3 pages.

Pines et al., "Hydrogenolysis of alcohols: II. Reduced nickel oxide—Its intrinsic acidity and catalytic activity in the conversion of alcohols to ethers", Journal of Catalysis, vol. 17, Issue 3, Jun. 1970, pp. 375-383.

International Preliminary Report on Patentability received for PCT Patent Application No. PCT/EP2021/060809, mailed on Nov. 17, 2022, 7 pages.

Maier et al., "Heterogeneous Catalysis, IV. Direct Reduction of Alcohols to Hydro-Carbons" Zeitschrift Fuer Naturforschung. Teil B, Anorganische Chemie, Organische Chemie, Verlag der Zeitschrift Fuer Naturforschung, vol. 37B, No. 3, Jan. 1, 1982, pp. 392-394.

International Search Report and Written Opinion received for PCT Patent Application No. PCT/EP2021/060809, mailed on Jul. 12, 2021, 9 pages.

Fang-Fang, et al. "Effect of Alcohol Addition on Fischer-Tropsch Synthesis over Cobalt-Based Catalysts", Acta Physico-Chimica Sinica, vol. 29, Issue 5, May 15, 2013, pp. 1063-1072.

* cited by examiner

CONTINUOUS PROCESS FOR THE PRODUCTION OF ALKANES

CROSS-REFERENCE TO RELATED APPLICATIONS

This application is a national stage application (under 35 U.S.C. § 371) of PCT/EP2021/060809, filed Apr. 26, 2021, which claims benefit of European Application No. 20173243.5, filed May 6, 2020, both of which are incorporated herein by reference in their entirety.

This invention relates to a continuous reductive dehydroxymethylation process for the preparation of alkanes from primary aliphatic alcohols, having 3 to 25 carbon atoms, in the presence of hydrogen and a catalyst in a reactor.

STATE OF THE ART

Respective alkanes can be used for example in decorative cosmetics and in care formulations as taught for instance in WO 2007/068371 A1 (BASF SE).

WO 2007/068371 A1 (BASF SE) also describes a process for the production of hydrocarbons from fatty alcohols by means of reductive dehydroxymethylation, which is conducted in the liquid phase (cf. Example 2). There is no mention of conducting the reaction in the vapor phase.

DE 10 2010 033 523 A1 (Saltigo GmbH) teaches a process for producing linear, saturated alkanes from primary linear alcohols of formula R—OH, where R represents a straight-chain saturated linear alkyl radical having 8 to 24 carbon atoms, by dehydroxymethylation of the primary alcohols in the presence of a ruthenium catalyst and hydrogen at a pressure in the range from 50 to 150 bar and a temperature in the range from 150° C. to 250° C. The dehydroxymethylation is conducted in the liquid phase (cf. Examples 1 and 2). There is no mention of conducting the reaction in the vapor phase.

A catalytic one step procedure for the C(1), C(2)-bond cleavage of long-chain aliphatic alcohols using as examples undecanol or dodecanol in a continuous flow tubular reactor using a Ni/Cu catalyst is taught in Helvetica Chimica Acta—Vol. 60, Fasc. 8 (1977)—Nr. 290. This Article is silent on whether the reaction is conducted in the vapor or in the liquid phase nor does is explicitly teach a reaction pressure.

The catalytic dehydrogenation of fatty alcohols is described by Elmer J. Badin in an Article entitled: "Catalytic Dehydrogenation I. Catalytic Conversion of Alcohols into Aldehydes, Paraffins and Olefins" in Journal of the American Chemical Society, Vol. 65, No. 10, 1943, pp. 1809-1813. The process in question is carried out in the liquid phase at atmospheric pressure and gives only poor yields of paraffins.

Operation in the liquid phase on a large scale constitutes a safety risk because it is strongly exothermic. This risk can be reduced by operating a huge liquid recycle stream, which renders the application of such a process technically more demanding and therefore economically less interesting.

It is known from the Article by Hermann Pines and T. P. Kobylinski entitled: "Hydrogenolysis of Alcohols" in Journal of Catalysis 17, 375-383 (1970) that neopentyl alcohol inter alia can be converted into isobutane. The reaction of butanol to propane in the presence of nickel catalysts in a hydrogen atmosphere is also described. However, the predominant products are the respective ethers. The use of long-chain fatty alcohols for such reactions is not mentioned. The reactions are conducted in the vapor phase but only at atmospheric pressure and are not carried out on an industrial scale, but only on a "micro" scale.

The reductive dehydroxymethylation of primary organic alcohols is also described in the Article by W. F. Maier, I. This and P. Schleyer entitled: "Direct Reduction of Alcohols to Hydrocarbons" in Zeitschrift für Naturforschung, Part B, 1982, 37B(3). No long-chain fatty alcohols are disclosed or suggested as suitable educts. The reactions are conducted in the vapour phase but only at atmospheric pressure and are not carried out on an industrial scale, but only on a "micro" scale.

GB 1,051,826 describes a process for the production of a primary monohydric alcohol by the removal of a hydroxymethyl group from a dihydric alcohol with nickel catalysts in a hydrogen atmosphere. According the examples presented in such application, the reaction is conducted in the liquid phase. There is no mention of conducting the reaction in the vapor phase.

TECHNICAL PROBLEM

The technical problem to be solved by the present invention was to improve existing processes for the production of alkanes form corresponding primary alcohols, and to remedy one or more disadvantages of the prior art, especially the above-mentioned disadvantages. The intention was to find a process to be performed with high conversion, high yields, including space-time yield, and selectivity. In addition, it was intended to find a process having a low safety risk.

Surprisingly it has been found, that the technical problem as specified above can be solved by a continuous reductive dehydroxymethylation process for the preparation of alkanes from primary aliphatic alcohols, having 3 to 25 carbon atoms, in the presence of hydrogen and a catalyst in a reactor at a pressure of 2 bar, that is characterized in that the dehydroxymethylation takes place in the vapor phase.

Unless explicitly taught otherwise any reference to pressure in the context of the present invention refers to the absolute pressure.

It was surprising that conducting the process at pressures 2 bar results in increased selectivity, as there is no corresponding hint in the art. The highest pressure taught in the art for dehydroxymethylation is 1 bar according to the above cited article by W. F. Maier et al.

Conducting the process in the vapor phase reduces the safety risk. It was surprising, that long chain primary alcohols, having a considerably high boiling point, can be evaporated even in high concentrations at high pressure of 2 bar as there is no hint in the art. As mentioned in the preceding paragraph, the highest pressure taught in the art is 1 bar.

When carrying out the reaction in the liquid phase, a liquid recycle stream needs to be operated in order to account for the fact, that the reaction is highly exothermic. No such liquid recycle stream needs to be operated when the reaction is conducted in the vapor phase. For the vapor phase process according to the present invention, the liquid hold-up of the respective alcohol is far smaller in the reactor than in case of a liquid phase process. It is also possible to operate at lower pressures as compared to those commonly used in the liquid phase. Thus, the risk of thermal explosion, rupture of the reactor and release of flammable products is much lower.

Thus, the safety risk is lower as compared to an operation of the process in the liquid phase.

DETAILED DESCRIPTION OF THE INVENTION

Without wanting to be bound by any theory or limiting the scope of the present invention in whatsoever kind, it is believed that the reductive dehydroxymethylation occurs as follows (exemplarily shown for dodecan-1-ol):

In the first step the alcohol is dehydrogenated. The resulting aldehyde is decarbonylated to give the desired alkane.

It is generally advantageous if the carbon monoxide resulting from the reductive dehydroxymethylation is hydrogenated to methane.

It is believed that the methanation occurs as follows:

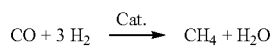

The water thus formed evaporates and does not adversely affect the course of the reductive dehydroxymethylation. Consequently, no specific measures need to be taken in order to remove it from the reaction mixture.

As a consequence, the CO content in the reactor is considerably low. Thus, catalyst lifetime can be increased by preventing CO poisoning. This is particularly advantageous, when the process is operated in a recycle gas mode. Operating the process in a recycle gas mode without converting the carbon monoxide into methane would result in a rapid accumulation of CO in the reactor bearing the risk of rapid catalyst poisoning. Catalyst lifetime for a process operated in a recycle gas mode can therefore be significantly increased, when carbon oxide is converted into methane.

In the light of a low CO content in the reactor, a catalyst is preferably used that can catalyze both, the reductive dehydroxymethylation of the primary alcohols and the hydrogenation of carbon monoxide (CO) resulting from the reductive dehydroxymethylation to methane ($CH_4$). That can be in principle any catalyst that has strong hydrogenation activity, for instance a platinum, palladium, ruthenium or nickel containing catalyst. A catalyst containing nickel is preferred. The catalyst preferably contains 10% by weight, particularly 20% by weight, more particularly 30 to 90% by weight, very particularly 40 to 80% by weight, of Ni.

The composition of the catalyst (in % by weight) is based on the total mass of the catalyst.

Such Ni catalyst may also be a supported catalyst. Preferably it contains 20 to 80% by weight of Ni and 20 to 80% by weight of a support, particularly 30 to 80% by weight of Ni and 20 to 70% by weight of a support, more particularly 40 to 80% by weight of Ni and 20 to 60% by weight of a support, very particularly 50 to 80% by weight of Ni and 20 to 50% by weight of a support.

Preferably the amount of Ni and support in the respective catalyst is 80 to 100% by weight, particularly 90 to 100% by weight, more particularly 95 to 100% by weight, very particularly 97 to 100% by weight.

Preferably the support is $Al_2O_3$ or $SiO_2$ or a mixture of both, $SiO_2$ being particularly preferred.

In the light of a low CO content in the reactor, it is also possible to conduct the reductive dehydroxymethylation in a first reactor containing a first catalyst and the methanation of the resulting CO in a second reactor containing a second catalyst. The first catalyst can be any catalyst that has sufficient activity for catalyzing the reductive dehydroxymethylation but that does not have sufficient activity for catalyzing the methanation. The second catalyst can be any catalyst that has sufficiently strong hydrogenation activity to catalyze the hydrogenation of carbon monoxide (CO) resulting from the reductive dehydroxymethylation to methane ($CH_4$).

The first catalyst can be for instance a copper containing catalyst. The second catalyst can be for instance a platinum, ruthenium, palladium or nickel containing catalyst. Preferably any of the nickel catalysts as specified above.

If the reaction is conducted in a recycle gas mode (as further outlined below) it is possible to use either a catalyst that can catalyze both, the reductive dehydroxymethylation of the primary alcohols and the hydrogenation of carbon monoxide (CO) resulting from the reductive dehydroxymethylation to methane ($CH_4$) (alternative 1) or to conduct the reductive dehydroxymethylation in a first reactor containing a first catalyst and the methanation of the resulting CO in a second reactor containing a second catalyst (alternative 2). In alternative 2 the gas recycle occurs after CO has been converted into methane in the second reactor. Otherwise CO would be recycled to the first reactor where it could cause rapid deactivation of the catalyst due to its poisoning with CO. Alternative 1 is preferred.

For either alternative, all preferred features as taught herein, including but not limited to those relating to pressure, temperature, catalyst hourly space velocity, starting material (alcohol), molar ratio of hydrogen and alcohol, are also preferred. Unless explicitly taught otherwise, in case of alternative 2, all respective preferred features equally refer to both reaction steps, i.e. reductive dehydroxymethylation and methanation.

The above teaching shall not in any way be construed as a limitation of the number of reactors to be used in either alternative. E.g. for alternative 1, it is also possible to use more than one reactor each of which is equipped with a respective catalyst that catalyzes reductive dehydroxymethylation and methanation. The conditions under which each reactor is operated can be different, especially the temperature may vary significantly. For alternative 2 it is for instance possible that reductive dehydroxymethylation is conducted in more than one reactor equipped with a respective catalyst. In the same way it is also possible that more than one reactor equipped with a respective catalyst is used for the methanation. Again, the conditions under which the reactors filled with different catalysts are operated, can vary.

The process according to the invention can be conducted at a pressure of 2 to 50 bar, particularly 5 to 40 bar, more particularly 8 to 35 bar, very particularly 11 to 25 bar. A pressure of above 50 bar is less preferred as there is no significant increase in selective but increased technical effort is required to handle the process at such high pressures.

The reaction temperature is preferably 100 to 350° C., particularly 150 to 300° C., more particularly 200 to 280° C. and very particularly 210 to 260° C.

The process may be carried out in isothermal or adiabatic fashion. An isothermal operating mode may be achieved, for example, by removing the reaction enthalpy liberated during the reaction in the reactor/in the reactors via suitable internal or external cooling devices. In the context of the present invention essentially isothermal conditions are to be understood as meaning that the temperature inside the reactor along the axis increases by no more than 6° C., preferably by no more than 3° C. The temperature difference is determined from the temperature at the reactor outlet and the temperature at the reactor inlet.

Depending on the operating conditions of the reactor it is possible to go from a purely isothermal operating mode (with the abovementioned temperature increase) towards an adiabatic operating mode where the temperature increase in the reactor may then be up to 50° C. for example.

For an adiabatic operating mode the reaction enthalpy liberated is not removed but rather remains in the reaction mixture. When the reaction is carried out in one or more fixed bed reactor an adiabatic process mode results in the reaction mixture increasing in temperature by up to 50° C. or more during passage through the reactor depending on the reaction conditions employed. To control and monitor the temperature the reactor/the reactors may have a plurality of measuring points/(thermowells) installed therein.

Conducting the dehydroxymethylation in the vapor phase is preferably achieved by evaporating the alcohol in a hydrogen containing gas stream and feeding it into the reactor in gaseous form. Unless explicitly stated otherwise, any reference to hydrogen shall mean molecular hydrogen ($H_2$). The hydrogen containing gas stream serves to evaporate the alcohol. In addition, the hydrogen contained therein serves as a reactant. In order to evaporate the alcohol, the hydrogen containing gas stream preferably has a flow-rate of 250 to 60000 $L_s$ per liter of catalyst and hour, preferably 480 to 53000 $L_s$ per liter of catalyst and hour more preferably 1200 to 45000 $L_s$ per liter of catalyst and hour. $L_s$ means volume in liters under standard conditions (p=1 atm, T=0° C.).

The evaporation can for instance be conducted in a liquid feed evaporator, a heating coil or a crossflow heating device.

The hydrogen containing gas stream can essentially consist of hydrogen. Preferably it contains 95 to 100 vol %, particularly 97 to 99.5 vol % hydrogen. The composition (in vol %) is based on the total volume of all gaseous components. In such embodiments the process is not operated in the recycle gas mode.

Preferably the process is operated in a recycle gas mode. Recycle gas mode does mean that gas is continuously recycled to the reactor.

The recycle gas stream can have a flow rate of 200 to 50000 $L_s$ per liter of catalyst and hour, preferably 400 to 45000 $L_s$ per liter of catalyst and hour more preferably 1000 to 40000 $L_s$ per liter of catalyst and hour.

In the context of this invention, recycle gas shall mean the gas stream that is recycled to the reactor before the addition of fresh hydrogen and before evaporating the alcohol. The recycle gas can be used to evaporate the alcohol. In those embodiments the recycle gas constitutes the hydrogen containing gas stream. It is also possible to combine the recycle gas with fresh hydrogen and using the combined streams to evaporate the alcohol. In those embodiments, the recycle gas together with the fresh hydrogen stream constitute the hydrogen containing gas stream.

Most preferably the process is operated in a recycle gas mode, whereby, after condensation of the alkanes and water from the reaction mixture, the resulting gaseous effluent is partially discharged and the remainder is recycled to the reactor as the recycle gas stream, whereby a fresh hydrogen stream is continuously fed into the process and whereby either the recycle gas stream alone or the recycle gas stream together with the fresh hydrogen stream constitute a hydrogen containing gas stream that is used to evaporate the alcohol. Preferably the recycle gas stream together with the fresh hydrogen stream constitute the hydrogen containing gas stream. It is advantageous to partially discharge the said resulting gaseous effluent, because if continuously fresh hydrogen is added, the overall gas stream to be handled would constantly increase. At a certain point in time, it would not be possible anymore to technically handle the amount of gas to be processed.

A possible set-up for the recycle gas mode is further exemplified in FIG. 1. In case the fresh hydrogen is added via lines 3a, 3b or 3c, the recycle gas stream together with the fresh hydrogen stream constitute a hydrogen containing gas stream that is used to evaporate the alcohol. In case the fresh hydrogen is added via line 3d, the recycle gas stream alone constitutes a hydrogen containing gas stream that is used to evaporate the alcohol.

The recycle gas stream can have a flow rate of 200 to 50000 $L_s$ per liter of catalyst and hour, preferably 400 to 45000 $L_s$ per liter of catalyst and hour more preferably 1000 to 40000 $L_s$ per liter of catalyst and hour and the fresh hydrogen stream can have a flow rate of 50 to 10000 $L_s$ per liter of catalyst and hour, preferably 80 to 8000 $L_s$ per liter of catalyst and hour more preferably 200 to 5000 $L_s$ per liter of catalyst and hour. $L_s$ means volume in liters under standard conditions (p=1 atm, T=0° C.). Preferably, the amount of fresh hydrogen is adjusted to the amount of alcohol fed to the catalyst, the minimum molar ratio being 2:1 in order to ensure complete hydrogenation of CO to methane.

The recycle gas stream preferably can have a composition as follows: 5 to 90 vol % hydrogen, 5 to 90 vol % methane and equal or less than 5 vol % other compounds, preferably 10 to 90 vol % hydrogen, 10 to 90 vol % methane and less than 2 vol %, particularly less than 1 vol % other compounds. The composition (in vol %) is based on the total volume of all gaseous components under standard conditions (p=1 atm, T=0° C.). The composition of the recycle gas can be analyzed by gas chromatography (gas chromatography on molecular sieve as stationary phase, thermal conductivity detection, quantification with external standard).

Other compounds are for instance molecular oxygen, molecular nitrogen, low boiling alkanes such as ethane, propane, or n-butane. The content of CO is usually less than 0.1 vol %, preferably less than 0.05 vol %, or even less than 0.03 vol %.

The fresh hydrogen stream usually essentially consists of hydrogen. Preferably it contains 95 to 100 wt.-%, particularly 97 to 99.5 wt.-% hydrogen. The composition (in % by weight) is based on the total mass of all gaseous components.

Preferably, the molar ratio of hydrogen and alcohol is 2 to 400, particularly 6 to 200, more particularly 7 to 50, very particularly 8 to 30 or even 6 to 20, 7 to 15 or 8 to 10.

In case the process is operated in a recycle gas mode, molar ratio means molar ratio of fresh hydrogen and alcohol. Due to the presence of hydrogen in the recycle gas the effective molar ratio in the reactor can be higher. Effective molar ratio refers to the molar ratio of hydrogen and alcohol, taking into account both, the amount of hydrogen in the fresh hydrogen stream as well as in the recycle gas stream. The amount of hydrogen in the recycle gas can be analyzed for instance by means of gas chromatography as specified above.

The effective molar ratio of hydrogen and alcohol can be 2 to 500, particularly 20 to 300, more particularly 40 to 200, very particularly 60 to 100. These ranges can be realized, when the recycle gas cycle stream has any of the preferred flow rates as specified above and the molar ratio of hydrogen and alcohol is selected according to the preferred range as specified above.

The process is carried out in a suitable reactor/suitable reactors. Preferred reactors are tubular reactors. Examples of suitable reactors with recycle gas stream can be found in Ullmann's Encyclopedia of Industrial Chemistry, $5^{th}$ Ed., Vol. B4, pages 199-238, "Fixed-Bed Reactors". Alternatively, the reductive dehydroxymethylation is advantageously carried out in a tube bundle reactor or in a single-stream plant. In a single stream plant, the tubular reactor in which the reaction proceeds can consist of a plurality (e.g. two or three) of individual tubular reactors connected in series.

The catalyst is usually used as shaped catalyst bodies; for example as tablets, spheres, rings, extrudates (e.g. strands). The catalyst is preferably arranged in the reactor as a fixed bed. It is possible for the flow towards the fixed catalyst bed to be either from the top or from the bottom.

When the catalyst is arranged as a fixed bed, it may be advantageous for the selectivity of the reaction to mix the catalyst with inert packings in order to "dilute" it. The proportion of packings in such catalyst preparations may be 20 to 80 vol %, particularly 30 to 60 vol % and in particular 40 to 50 vol %.

The mass hourly space velocity is 0.05 to 2 kg, preferably 0.1 to 1 kg, more preferably 0.15 to 0.8, or even 0.2 to 0.65 kg alcohol per liter of catalyst (bed volume) and hour.

The process is usually carried out in a way so that the conversion of the alcohol is in the range of 80 to 100%, particularly 90 to 100%, more particularly 95 to 100%, very particularly 98 to 100%.

The process according to the present invention is suited for the reaction of primary aliphatic alcohols, having 3 to 25, preferably 8 to 24 carbon atoms. In the context of this invention primary aliphatic alcohol is also referred to as "primary alcohol" or "alcohol". The term "aliphatic" shall mean any functionalized or unfunctionalized organic residue that contains no aromatic ring system. It can have any functional group.

The primary alcohol may be a fatty alcohol having 8 to 24 carbon atoms. It may be produced in known manner from renewable raw materials, such as coconut oil, palm oil or palm kernel oil for example, by transesterification with methanol or saponification with strong bases (e.g. KOH or NaOH) or acids and subsequent hydrogenation. Besides pure fatty alcohols, other linear or branched, monohydric or polyhydric alcohols, alcohol mixtures or derivatized alcohols, having 3 to 25, preferably 8 to 24 carbon atoms produced on an industrial scale may also be used in principle and are preferred. The use of fatty alcohols with even-numbered C chains is particularly preferred because the odd-numbered alkanes otherwise so difficult to produce can readily be obtained in this way.

Preferably the alcohol is a fatty alcohol having the generic formula R—$CH_2$—OH in which R is $C_7$-$C_{23}$-alkyl, particularly $C_7$-$C_{17}$-alkyl, more particularly $C_9$-$C_{15}$-alkyl, very particularly $C_{11}$-$C_{15}$-alkyl.

In a preferred embodiment, such alcohol is a linear fatty alcohol. Thus, in the generic formula mentioned above, R being linear $C_7$-$C_{23}$-alkyl, particularly linear $C_7$-$C_{17}$-alkyl, more particularly linear $C_9$-$C_{15}$-alkyl, very particularly linear $C_{11}$-$C_{15}$-alkyl.

For the same reason as outlined above, the use of respective fatty alcohols with an even number of C atoms are preferred. Thus, preferably the alcohol is a fatty alcohol having the generic formula R—$CH_2$—OH in which R is $C_7$-, $C_9$-, $C_{11}$-, $C_{13}$-, $C_{15}$-, $C_{17}$-, $C_{19}$-, $C_{21}$-, $C_{23}$-alkyl, particularly $C_7$-, $C_9$-, $C_{11}$-, $C_{13}$-, $C_{15}$-, $C_{17}$-alkyl, more particularly $C_9$-, $C_{11}$-, $C_{13}$-, $C_{15}$-alkyl, very particularly $C_{11}$-, $C_{13}$-, $C_{15}$-alkyl.

Among such fatty alcohols, having an even number of C atoms, those being linear, are particularly preferred. Thus, preferably the alcohol is a fatty alcohol having the generic formula R—$CH_2$—OH in which R is linear $C_7$-, $C_9$-, $C_{11}$-, $C_{13}$-, $C_{15}$-, $C_{17}$-, $C_{19}$-, $C_{21}$-, $C_{23}$-alkyl, particularly linear $C_7$-, $C_9$-, $C_{11}$-, $C_{13}$, $C_{15}$-, $C_{17}$-alkyl, more particularly linear $C_9$-, $C_{11}$-, $C_{13}$-, $C_{15}$-alkyl, very particularly linear $C_{11}$-, $C_{13}$-, $C_{15}$-alkyl.

It is also possible to use mixtures of any of the primary alcohols specified above.

In a very preferred embodiment the process according to the present invention is used for preparing undecane and tridecane by reductive dehydroxymethylation of dodecan-1-ol and tetradecane-1-01.

The alkanes produced in accordance with the invention may be used for the production of cosmetic formulations such as, for example, hair shampoos, hair lotions, foam baths, shower baths, creams, gels, lotions, alcoholic and aqueous/alcoholic solutions, emulsions, wax/fat compounds, stick preparations, powders and ointments. These preparations may contain as further auxiliaries and additives mild surfactants, oil components, emulsifiers, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosine inhibitors (depigmenting agents), hydrotropes, solubilizers, preservatives, perfume oils, dyes and the like. The alkanes are preferably used as oil components.

By virtue of the present invention, it is specifically possible to produce alkanes with a particular chain length as individual components in cosmetic formulations as so-called light emollients or even to mix them in a particular manner in order to be able to establish special properties such as, for example, spreading behavior, volatility or even flash points. More particularly, the possibility of mixing the alkanes on the building block principle affords major advantages over alkanes from petrochemical sources which are almost exclusively present as complex mixtures of branched and unbranched hydrocarbons. In cases such as these, further working up by distillation is only possible with considerable effort or would be attended by the problem of residues of unwanted isomers remaining in the product. In addition, the toxicological evaluation of a defined hydrocarbon or a defined hydrocarbon mixture, which is particularly important for cosmetic applications, is very much simpler and safer.

Therefore, the present invention also relates to a process for the production of a cosmetic formulation characterized in that one or more alkanes are prepared according to any of the preceding claims and the resulting alkane/alkanes is/are mixed with one or more other compounds in order to obtain the cosmetic formulation.

FIG. 1 represents an embodiment that is particularly preferred. Alcohol via line (1) and recycle gas via line (2) are fed into saturator (4). The recycle gas is passed through compressor (11) in order to increase its pressure to the desired reaction pressure. Fresh hydrogen can be fed directly into the saturator (4) via line (3a) or it can be fed into the recycle gas via line (3b). It can also be fed into the recycle gas, before the latter is passed through the compressor (11). This is advantageous because the hydrogen stream has a higher pressure than the recycle gas, thus reducing the amount of energy required by the compressor. Hydrogen can also be fed directly into the reactor via line (3d). Theoretically, a combination of such ways to add the hydrogen (i.e. (3a) to (3d)) is also possible. In the saturator (4) the alcohol is evaporated, and the resulting gaseous stream is fed into the reactor (6) via line (5). The reaction mixture is passed through heat exchanger (8) and optionally through a cryostat via line (7), where it is cooled down and fed into high pressure separator (9) where a gaseous effluent, consisting essentially of hydrogen and methane, is withdrawn. Via line (10) said gaseous effluent is partly discharged. The remainder is recycled via line (2) to saturator (4) as the recycle gas stream. The crude reaction product from high-pressure separator (9) is fed via line (12) into low-pressure separator (13) where it is further degassed. The resulting gaseous stream, consisting essentially of hydrogen and methane, is discharged via line (15). The crude reaction product, in particular value product alkane and high boilers are withdrawn form low-pressure separator (13) via line (14). Said crude alkane product can be subjected to further purification The following examples only serve for the purpose of the illustration of the present invention and shall therefore not limit it in whatsoever kind.

EXAMPLES

The experiments were carried out in a vapor phase reactor in continuous mode (bottom-up flow). The reactor was comprised of an oil-heated 2.1 m double-walled tube with 4.11 cm inner diameter which was filled from bottom to top with 40 mL of ceramic rings (2.5-3.5 mm diameter), 0.5 L catalyst (60 wt-% Nickel on $SiO_2$ (40 wt-%), BASF SE) and 1.8 L ceramic rings (2.5-3.5 mm diameter). After the filling the catalyst was activated by exchanging nitrogen with hydrogen and heating to 280° C. (circulated oil temperature) in a stream of hydrogen of 200 $L_s$/h ($L_s$=volume in liters under standard conditions (p=1 atm, T=0° C.)) for 24 h.

The feeds of make-up hydrogen, recycle gas and Lorol were heated to the required temperature and fed to the liquid feed evaporator The oil thermostat of the double-walled reactor tube was set to the desired reactor temperature. Via two heat exchangers the reactor output was first cooled with cooling water, then by means of a cryostat cooled to 10° C. and fed into a high-pressure separator. There, separation into liquid and vapor phase was carried out. The liquid phase was depressurized into a low-pressure separator that was maintained at a temperature of 30° C. and from which remaining gaseous components were vented to a flare and the liquid discharged into a collecting vessel for crude reactor output. Via a gas compressor, the vapor phase from the high-pressure separator was recycled in a defined amount and was used as carrier gas for the feed. Via a pressure control valve excess gas was discharged into the flare for burning. Conversion and selectivity of the crude output were determined by gas chromatography.

Liquid feed evaporator and reactor were all set to 230° C. 300 $L_s$/h fresh make-up $H_2$ (corresponding to 600 $L_s$ per liter of catalyst and hour) and approximately 4000 $L_s$/h recycle gas (corresponding to 8000 Ls per liter of catalyst and hour) and 0.3 kg/h of Lorol were fed into the reactor. Lorol is a mixture of approx. 72 wt.-% of dodecanol and 26 wt.-% tetradecanol (containing approx. 2 wt.-% of other alcohols). The Lorol used in these experiments was obtained by hydrogenation of a corresponding mixture of lauric and myristic acid being derived from palm kernel oil and coconut oil. Said palm kernel oil has been sourced from Indonesia, Malaysia, and Columbia. Said coconut oil has been sourced from Indonesia and the Philippines. The pressure was varied as specified in table 1. The composition of the output including conversion and selectivity is given in table 1.

DISCUSSION OF RESULTS

Figure 2:
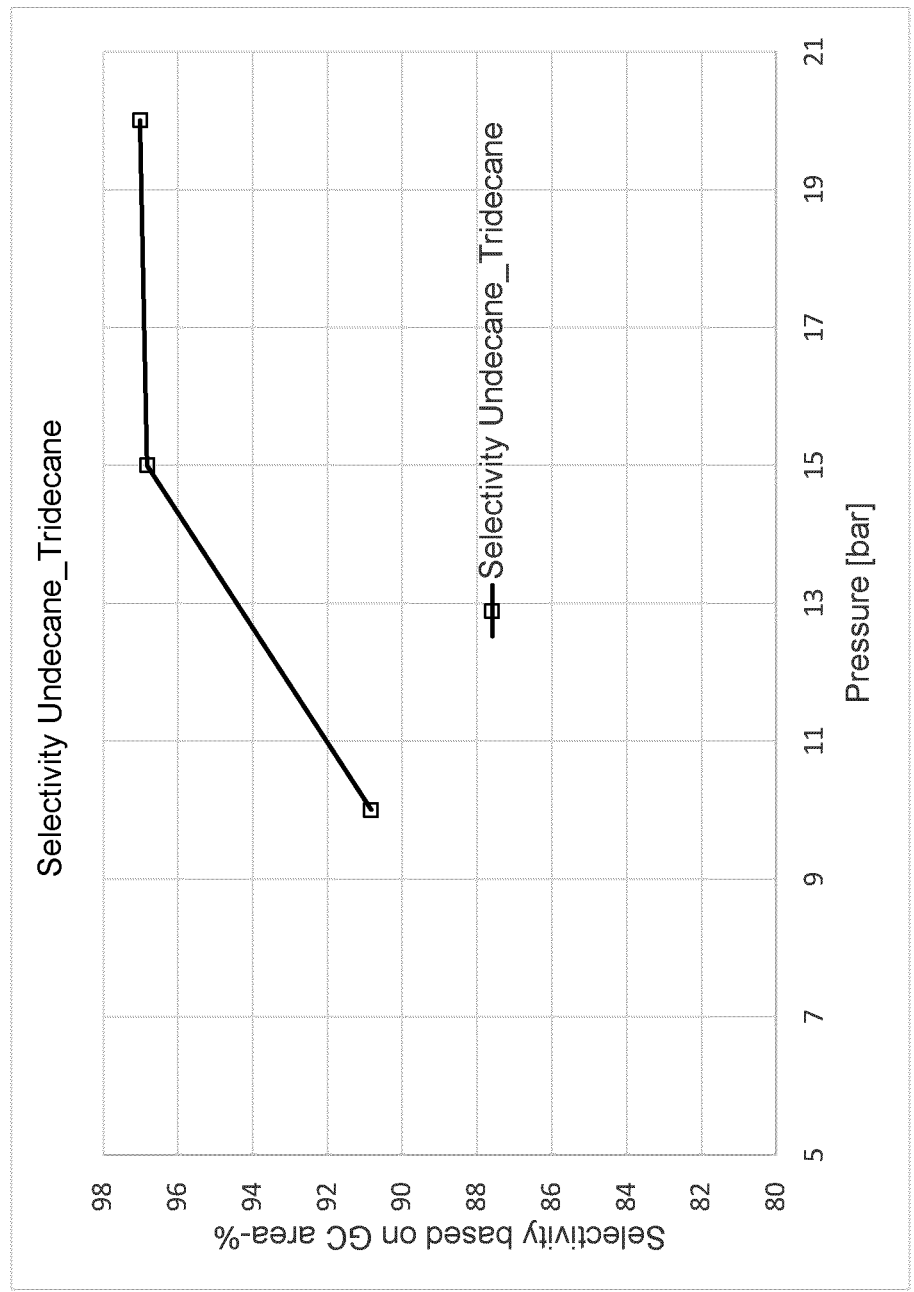

FIG. 2 is based on entries 1 to 3 of the table presented above. Selectivity dependency relating to the reaction pressure is visualized. There is a drop of selectivity when reaction pressure is decreased. Thus, a pressure lower than 2 bar gives lower selectivity than a pressure of 2 bar and higher.

TABLE 1

Results

| # | $T_{reactor\ (measured\ at\ exit)}$ [° C.] | Load [kg/L/h] | MR | RG [$10^3$ Ls/h] | p [bar] | C7 | C8 | C9 | C10 | C11 | C12 | C13 | Lorol | High boilers. | Others | Conv. [%] | Sel. [%] |
|---|---|---|---|---|---|---|---|---|---|---|---|---|---|---|---|---|---|
| | | | | | | | | | GC-area-% | | | | | | | | |
| 1 | 232 | 0.60 | 8 | 4.0 | 15 | 0.0 | 0.0 | 0.3 | 0.2 | 71.1 | 1.0 | 25.7 | 0.0 | 0.3 | 0.3 | 100.0 | 96.8 |
| 2 | 235 | 0.60 | 8 | 4.0 | 10 | 0.0 | 0.0 | 0.3 | 0.2 | 66.9 | 0.6 | 23.9 | 0.0 | 6.9 | 1.2 | 100.0 | 90.8 |
| 3 | 232 | 0.61 | 8 | 4.0 | 20 | 0.0 | 0.0 | 0.3 | 0.1 | 70.5 | 0.8 | 25.3 | 0.0 | 1.7 | 0.3 | 100.0 | 95.9 |

Load: Catalyst hourly space velocity in kg alcohol per liter of catalyst (bed volume) and hour.
MR: Molar ratio fresh $H_2$ to lorol
RG: Recycle gas
Conv.: Conversion of lorol
Sel.: Selectivity referring to valuable products undecane (C11) and tridecane (C13)

The invention claimed is:

1. A continuous reductive dehydroxymethylation process comprising preparing alkanes from primary aliphatic alcohols, having 3 to 25 carbon atoms, in the presence of hydrogen and a catalyst in a reactor at a pressure of ≥2 bar, wherein the dehydroxymethylation takes place in the vapor phase.

2. The process according to claim 1, wherein the pressure is 2 to 50 bar.

3. The process according to claim 1, wherein the alcohol is a fatty alcohol having the generic formula R—$CH_2$—OH in which R is $C_7$-$C_{23}$-alkyl.

4. The process according to claim 3, wherein the alcohol is a linear fatty alcohol.

5. The process according to claim 1, wherein the process is operated in a recycle gas mode.

6. The process according to claim 5, wherein the recycle gas stream has a flowrate of 200 to 50000 $L_s$ per liter of catalyst and hour.

7. The process according to claim 6, wherein the process is operated in a recycle gas mode, whereby, after condensation of the alkanes and water from the reaction mixture, the resulting gaseous effluent is partially discharged and the remainder is recycled to the reactor as the recycle gas stream, whereby a fresh hydrogen stream is continuously fed into the process and whereby either the recycle gas stream alone or the recycle gas stream together with the fresh hydrogen stream constitute a hydrogen containing gas stream that is used to evaporate the alcohol.

8. The process according to claim 1, wherein the catalyst hourly space velocity is 0.05 to 2 kg alcohol per liter of catalyst (bed volume) and hour.

9. The process according to claim 1, wherein the recycle gas stream has the following composition: 5 to 90 vol % hydrogen, 5 to 90 vol % methane and equal or less than 5 vol % other compounds.

10. The process according to claim 1, wherein the catalyst contains ≥10% by weight, of Ni.

11. The process according to claim 10, wherein the catalyst is a supported catalyst that contains 20 to 80% by weight of Ni and 20 to 80% by weight of a support.

12. The process according to claim 11, wherein the support is $Al_2O_3$ or $SiO_2$ or a mixture of both, $SiO_2$ being preferred.

13. The process according to claim 1, wherein the molar ratio of hydrogen and alcohol is 2 to 400.

14. The process according to claim 1, for preparing undecane and tridecane by reductive dehydroxymethylation of dodecan-1-ol and tetradecane-1-ol.

15. A process for the production of a cosmetic formulation wherein one or more alkanes are prepared according to claim 1 and the resulting alkane/alkanes is/are mixed with one or more other compounds in order to obtain the cosmetic formulation.

* * * * *